United States Patent
Sasahara et al.

[19]

[11] Patent Number: 6,127,822

[45] Date of Patent: Oct. 3, 2000

[54] ADHESIVE MEMBER FOR FORMING AN ADHESIVE LAYER BETWEEN TWO MEMBERS AND CAPABLE OF DETECTING AN INTERNAL DEFECT IN THE ADHESIVE LAYER

[75] Inventors: Jun Sasahara; Hajime Goto; Tadahiro Kubota, all of Saitama, Japan

[73] Assignee: Honda Giken Kogyo Kabushiki Kaisha, Tokyo, Japan

[ * ] Notice: This patent is subject to a terminal disclaimer.

[21] Appl. No.: 08/815,471

[22] Filed: Mar. 11, 1997

Related U.S. Application Data

[63] Continuation-in-part of application No. 08/381,687, Jan. 26, 1995, Pat. No. 5,640,088.

[30] Foreign Application Priority Data

| Jan. 26, 1994 | [JP] | Japan | 6-006771 |
| Feb. 21, 1994 | [JP] | Japan | 6-022826 |
| May 24, 1994 | [JP] | Japan | 6-109985 |

[51] Int. Cl.[7] .............. G01B 7/24; G01R 33/18; G01N 27/82

[52] U.S. Cl. .................................. 324/209; 324/240

[58] Field of Search .................... 324/209, 239, 324/240, 242; 73/763, 768; 340/675, 676; 198/810.01, 810.02

[56] References Cited

U.S. PATENT DOCUMENTS

| 3,834,524 | 9/1974 | Ratz et al. | 340/671 |
| 5,086,651 | 2/1992 | Westermo et al. | 324/209 |
| 5,194,806 | 3/1993 | Obama | 324/209 |
| 5,640,088 | 6/1997 | Sasahura et al. | 324/209 |

Primary Examiner—Walter E. Snow
Attorney, Agent, or Firm—Lyon & Lyon LLP

[57] ABSTRACT

An adhesive member is used to bond one member to another member to form an adhesive layer whose internal defection can be detected by utilizing a magneto-mechanical property of a soft magnetic material. The adhesive member is comprised of a main body formed of an uncured adhesive, and a plurality of soft magnetic materials embedded in the main body and restrained in an external force-applied state after curing of the main body.

22 Claims, 10 Drawing Sheets

Number of repetitions of stress cycle (times)

ADHESIVE MEMBER FOR FORMING AN ADHESIVE LAYER BETWEEN TWO MEMBERS AND CAPABLE OF DETECTING AN INTERNAL DEFECT IN THE ADHESIVE LAYER

CROSS REFERENCE TO RELATED APPLICATION

This is a Continuation-In-Part application of Ser. No. 08/381,687, filed Jan. 26, 1995, now U.S. Pat. No. 5,640,088.

BACKGROUND OF THE INVENTION

1. Field of the Invention

The present invention relates to an adhesive member for forming an adhesive layer whose internal defection is detectable, and particularly, to an adhesive member for bonding one member to another member to form an adhesive layer whose internal defection is detectable by utilizing a magneto-mechanical property of soft magnetic materials.

2. Description of the Related Art

Conventionally known adhesive layer estimating processes include a non-destructive test process such as an ultrasonic damage-detecting process, an X-ray process or the like, and a performance test process according to a weathering evaluation test process rule or the like defined in JIS (Japanese Industrial Specification)-K-6860.

However, when the non-destructive test process is applied to a test piece, a corresponding estimation is provided, but the non-destructive test process is unsuitable for an adhesive layer as described above, because it is accompanied by many limitations for the shape, the size and the like of the adhesive layer. On the other hand, the performance test process is one applied to only a test piece and hence, it is very difficult to estimate the adhesive layer between both the bonded members by this performance test process.

SUMMARY OF THE INVENTION

Accordingly, it is an object of the present invention to provide an adhesive member of the above-described type, which is capable of forming an adhesive layer whose internal defection can be easily detected in a non-destructive state.

To achieve the above object, according to the present invention, there is provided an adhesive member for bonding one member to another member to form an adhesive layer whose internal defection can be detected by utilizing a magneto-mechanical property of soft magnetic materials, the adhesive member comprising a main body formed of an uncured adhesive, and a plurality of soft magnetic materials embedded in the main body and restrained in an external force-applied state after curing of the main body.

When the one member is bonded to the other member by use of the adhesive member, the plurality of soft magnetic materials are embedded with a predetermined stress in the adhesive layer and hence, the stress of the soft magnetic materials can be measured with a good accuracy from the surface of either one of the bonded members by utilizing the magneto-mechanical property of the soft magnetic materials.

On the other hand, if internal defections such as cracks are produced in the cured main body in the adhesive layer, a restraining force acting on the soft magnetic materials, i.e., an external force originally applied thereto is decreased and hence, with this decrease, the stress of the soft magnetic materials is also decreased. Thus, the internal defections in the adhesive layer can be easily detected in a non-destructive state.

Immediately after both the members are bonded to each other, the stress of the soft magnetic materials is detected along the surface of either one of the bonded members. At this time, if an abnormal stress value is provided in a portion, such portion is considered to be a poorly bonded point. In this way, the adhesive member is also used to determine whether the adhesive layer formed from the adhesive member is sound or not.

For example, if the main body is formed of an uncured thermosetting synthetic resin-based adhesive and has an extremely small thickness, and both the members to be bonded have a thermal expansion coefficient different from that of the soft magnetic materials, the application of an external force to the soft magnetic materials is easily realized by a difference between the thermal expansion coefficients of the soft magnetic materials and both the bonded members during heating and curing of the main body. However, it is also possible to cure the main body in a state in which a tension has been applied to the soft magnetic materials.

In addition, according to the present invention, there is provided an adhesive member comprising a measuring coil wound around each of a plurality of soft magnetic materials, and there is also provided an adhesive member comprising a measuring coil wound around a single soft magnetic material having a zigzag shape.

With such arrangements, in measuring a stress of the soft magnetic material, the measuring coil can be used as an exciting coil and a detecting coil and hence, it is unnecessary to dispose other exciting and detecting coils outside the adhesive layer, which is advantageous when there is no space for disposing these coils, and when it is difficult to dispose the coils. In addition, since the measuring coil is embedded in the main body, the distance between the measuring coil and the soft magnetic materials is maintained substantially constant and thus, it is possible to further enhance the measuring accuracy and to improve the reproducibility thereof.

The above and other objects, features and advantages of the invention will become apparent from the following description of the preferred embodiments taken in conjunction with the accompanying drawings.

DETAILED DESCRIPTION OF THE PREFERRED EMBODIMENTS

Embodiment 1

Figure 1:
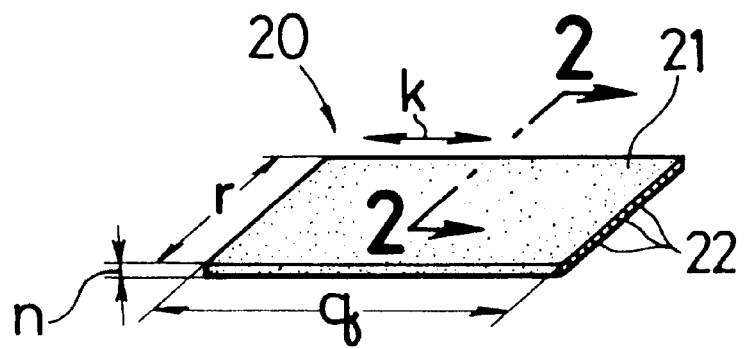
FIG. 1 is a perspective view of an adhesive member.
Figure 2:
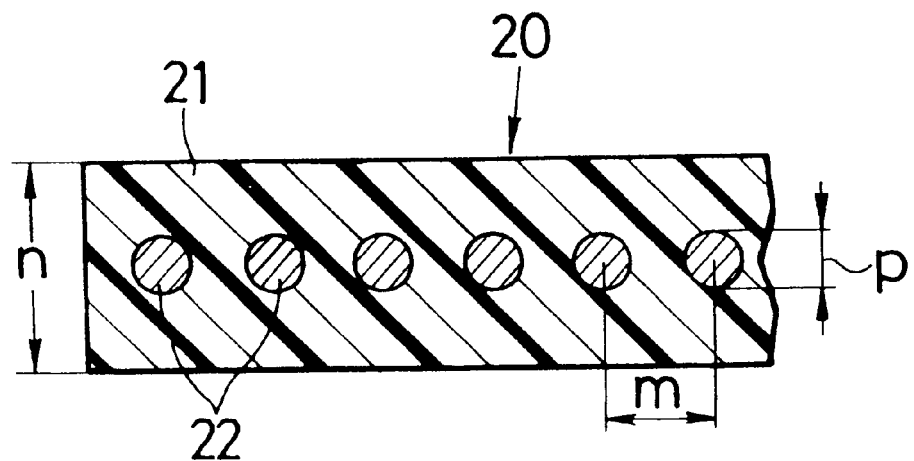
FIG. 2 is an enlarged sectional view taken along a line 2—2 in FIG. 1.

Referring to FIGS. 1 and 2, an adhesive layer forming adhesive member 20 whose internal defection is detectable is in the form of a rectangular film having a uniform thickness and comprised of a main body 21 formed of an uncured adhesive, and a plurality of fibrous soft magnetic materials 22 embedded in the main body 21.

A thermosetting synthetic resin-based adhesive is mainly used as the adhesive forming the main body 21. Preferred examples of such thermosetting synthetic resin-based adhesive are a phenolic resin-based adhesive, an epoxy resin-based adhesive, a phenol/epoxy resin-based adhesive and the like, from the viewpoint that these adhesives are easily formed into a film. However, a thermoplastic synthetic resin-based adhesive may be used as well.

The soft magnetic material 22 is made from an amorphous metal. The plurality of wires or fibers of soft magnetic materials 22 are arranged side-by-side at a constant pitch m in parallel to a lengthwise direction k of the main body 21.

The thickness n of the adhesive member 20 is suitably in a range of $0.03 \text{ mm} \leq n \leq 1.0 \text{ mm}$, and the diameter p of the soft magnetic material 22 is suitably in a range of $30 \mu\text{m} \leq p \leq 200 \mu\text{m}$. On the basis of these dimensions, the pitch m between the soft magnetic materials is set in a range of $2p \leq m \leq 10p$ in the relationship to the diameter p.

If the pitch m is set in such a range, the amount of the main body 21, i.e., the amount of the adhesive is suitable and hence, a sufficient adhesive strength can be obtained. In addition, since the distributed state of the soft magnetic materials 22 is suitable, a stress detecting sensitivity is improved. However, if m<2p, the volume fraction Vf of the soft magnetic materials 22 in the adhesive layer is nearly equal to 40% in relation to the thickness n of the adhesive member 20. For this reason, a deficiency of the adhesive strength is caused, and the soft magnetic materials 22 are liable to be entwined with one another during a bonding operation, thereby making it difficult to provide a uniform thickness of the adhesive layer. On the other hand, if m>10p, the distribution of the soft magnetic materials 22 is dispersed, resulting in a reduced stress detecting sensibility.

Table 1 shows the size, materials and the like in a particular example of the adhesive member 20. In Table 1, the volume fraction Vf of the soft magnetic materials 22 is given as a value in the adhesive member 20.

TABLE 1

| Size of adhesive member 20 | In FIG. 1, length q: 40 mm, width r: 25 mm, thickness n: 0.5 mm |
|---|---|
| Main Body | Material: epoxy resin-based adhesive (made by 3M Corp. under the trade name of AF-191) |
| Soft magnetic material 22 | Material: Amorphous alloy, $Fe_{77.5}Si_{7.5}B_{15}$ (unit of numeral values is % by atom), Coercive force Hc: 0.4 oersted, Thermal expansion coefficient: $7.3 \times 10^{-6}/°C.$, Diameter p: 125 μm, Pitch m: 0.3 mm (Vf - 8%) |

Figure 3:
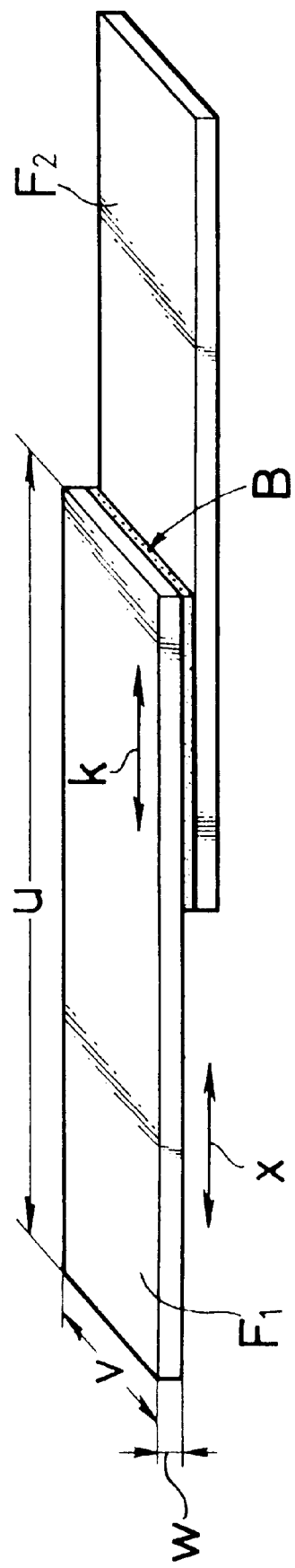
FIG. 3 is a perspective view showing two FRP members bonded to each other through an adhesive layer.

As shown in FIG. 3, two plate-like FRP members $F_1$ and $F_2$ having the same structure and the same size were prepared as members to be bonded. In these FRP members $F_1$ and $F_2$, the reinforcing fiber member is formed as a laminate produced by laminating eight cloths of carbon fiber having a diameter of 6 μm, so that the orientations of the carbon fibers in the adjacent cloths are offset by 45° from each other, and the matrix is formed of an epoxy resin. Each of the FRP members $F_1$ and $F_2$ has a length u of 155 mm, a width v of 25 mm, a thickness w of 1.6 mm, and a thermal expansion coefficient of $3.5 \times 10^{-6}/°C.$ In bonding the FRP members $F_1$ and $F_2$ together, the entire adhesive member 20 was clamped between one end of each of the FRP members $F_1$ and F2 in such a manner that the lengthwise direction k of the adhesive member 20 is matched with the lengthwise direction x of both the FRP members $F_1$ and $F_2$, and then, the adhesive member 20 was cured at 180° C. under 3.2 atmospheres for 1 hour. As a result, an adhesive layer B was formed, and the FRP members $F_1$ and $F_2$ were bonded to each other through the adhesive layer B. At this time, the adhesive margin area was 10 cm².

Figure 4:
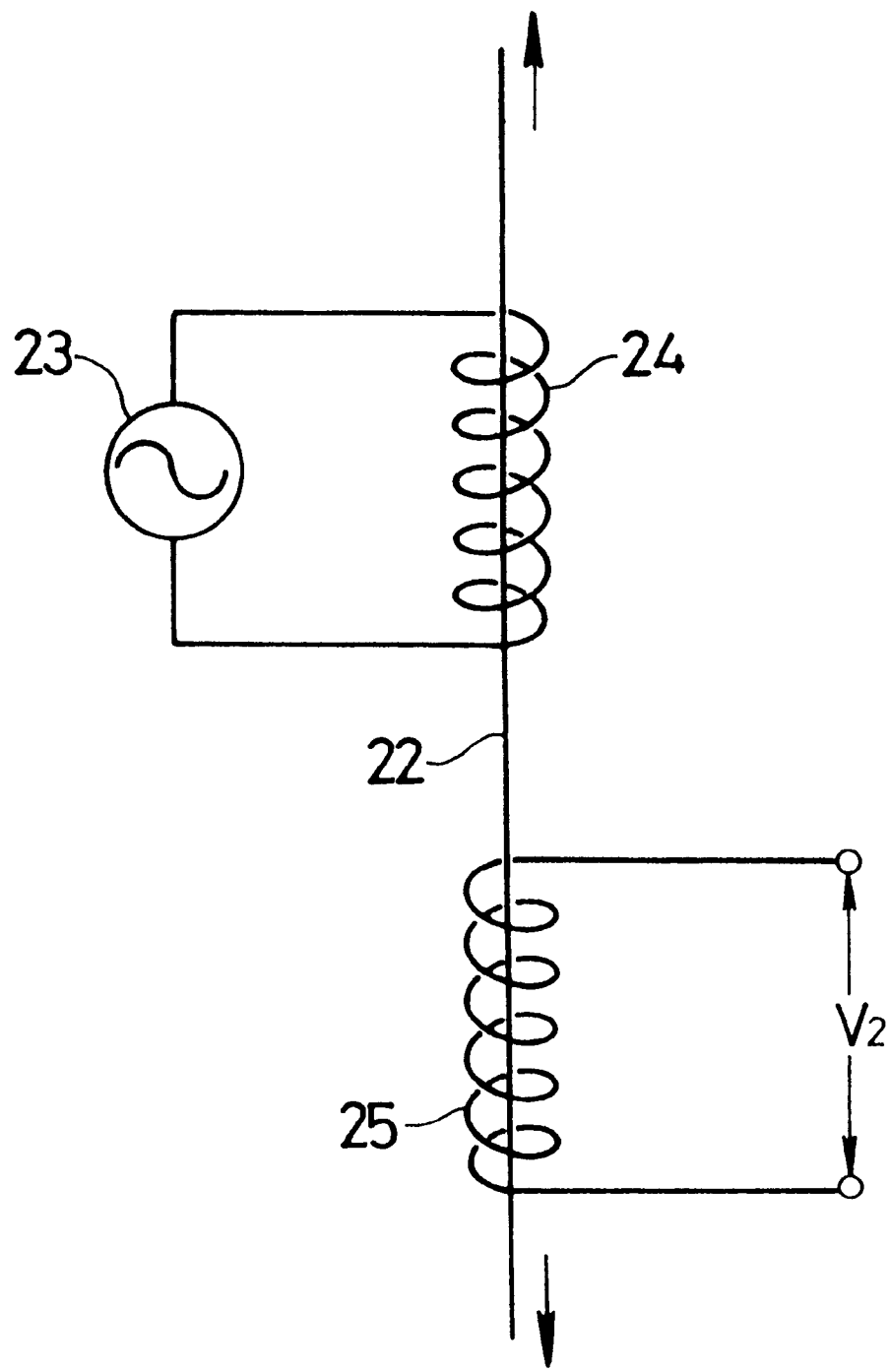
FIG. 4 is a diagram for explaining the principle of a stress measuring process.

In this case, the soft magnetic material 22 is restrained in a tension load-applied state at ambient temperature after heating/curing of the main body 21, i.e., after formation of the adhesive layer B, because the thermal expansion coefficient of the soft magnetic material 22 is $7.3 \times 10^{-6}/°C.$, and the thermal expansion coefficient of the FRP members $F_1$ and $F_2$ is $3.5 \times 10^{-6}/°C.$ When the stress of the soft magnetic materials 22 in the adhesive layer B is measured, the following procedure is employed, as shown in FIG. 4: an AC magnetic field exceeding the coercive force of the soft magnetic material 22 is applied to the soft magnetic material 22 to be measured by use of an exciting coil 24, thereby inducing an AC electromotive force in the detecting coil 25 through the soft magnetic material 22, and an effective value of one or more high harmonic wave components including a stress information of the soft magnetic material 22 in a wave form of the AC electromotive force, or a distortion rate K (hereinafter simply referred to as distortion rate K) calculated from such effective value and an effective value of a basic wave component is defined as a measurement amount.

The principle of this stress measuring procedure will be described below.

Referring to FIG. 4, the fibrous soft magnetic material 22 is inserted through an exciting coil 24 connected to an oscillator 23 and through a detecting coil 25, and a predetermined tension load is applied to the soft magnetic material 22.

When the oscillator 23 is operated to apply an AC magnetic field H including no D.C. magnetic field component and exceeding the coercive force Hc of the soft magnetic material 22 to the soft magnetic material 22 by the exciting coil 24, a positively and negatively symmetric AC electromotive force $V_2$ is induced in the detecting coil 25 through the soft magnetic material 22.

Here, the AC electromotive force $V_2$ is represented by the following equation (1):

$$V_2 = -\frac{d\phi}{dt} = -\alpha\left(1 + 4\pi\frac{dI}{dH}\right)\frac{dH}{dt} \tag{1}$$

wherein $\Phi$ is a magnetic bundle; t is a time; $\alpha$ is a factor; I is a intensity of magnetization of the soft magnetic material 22; and H is an intensity of the AC magnetic field.

The AC magnetic field H is represented by the following equation (2):

$$H = Hm \cdot \sin(2\pi fot + \phi o) \tag{2}$$

wherein Hm is an amplitude of the AC magnetic field; $f_0$ is a frequency; and $\phi_0$ is a phase angle.

Here, when the equation (2) is differentiated by the time t, the following equation (3) is obtained:

$$\frac{dH}{dt} = 2\pi foHm \cdot \cos(2\pi fot + \varphi o) \tag{3}$$

Thereupon, if dH/dt in the equation (1) is substituted by the equation (3), the AC electromotive force $V_2$ is represented by the following equation (4):

$$V_2 = -2\pi\alpha foHm\left(1 + 4\pi\frac{dI}{dH}\right)\cos(2\pi fot + \varphi o) \tag{4}$$

Figure 5:
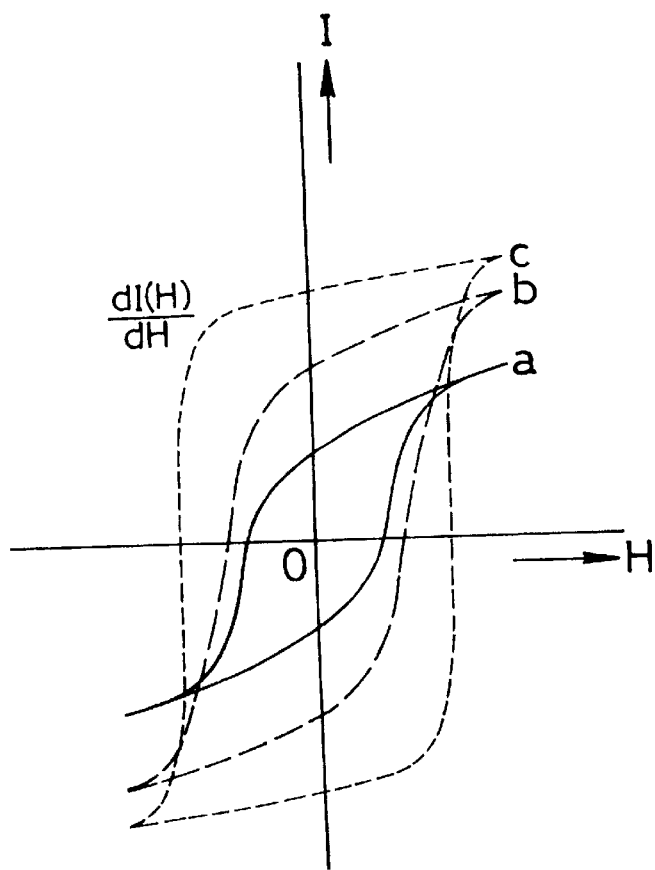
FIG. 5 is a diagram illustrating magnetization curves for a soft magnetic metallic wire.

In the course of magnetization of the soft magnetic material 22, a magnetization curve as shown by a line a in FIG. 5 is obtained and hence, the equation (4) is represented by the following equation (5) using an instantaneous magnetization rate dI (H)/dH:

$$V_2 = -2\pi\alpha foHm\left(1 + 4\pi\frac{dI(H)}{dH}\right)\cos(2\pi fot + \varphi o) \tag{5}$$

Figure 6:
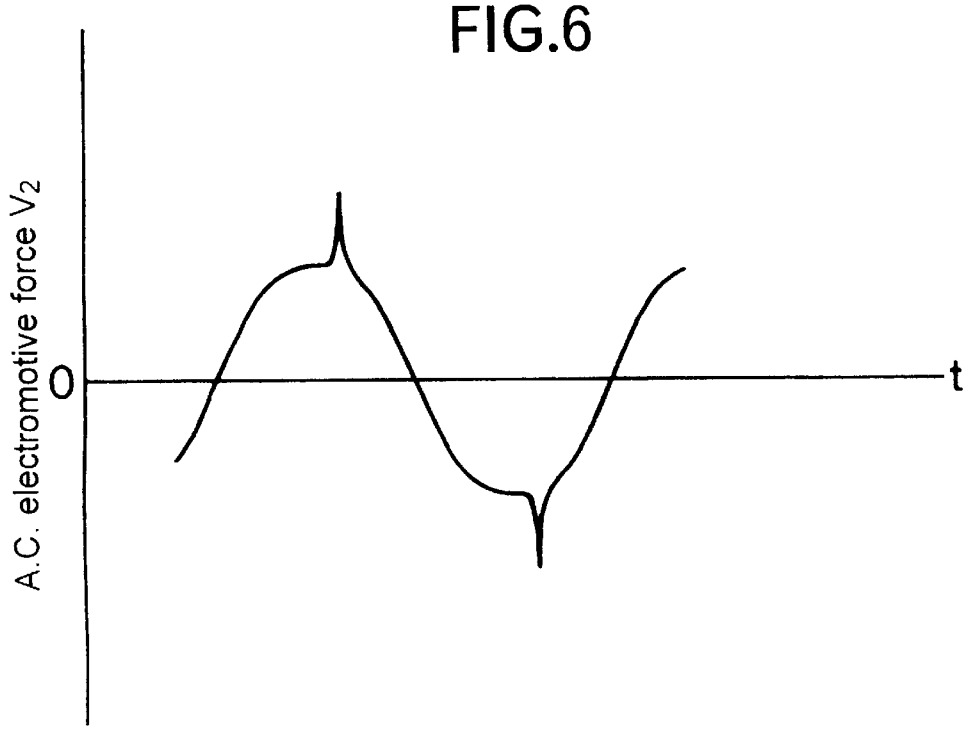
FIG. 6 is a diagram illustrating the wave form of an AC electromotive force $V_2$.

The AC electromotive force $V_2$ includes higher harmonic wave components, because its wave form is a distortion wave as shown in FIG. 6. In this case, the AC magnetic field H includes no DC magnetic field component and hence, such higher harmonic wave component of the AC electromotive force $V_2$ is comprised of only odd-numbered harmonic wave components and includes no even-numbered harmonic wave component.

The higher harmonic wave component depends on the instantaneous magnetization rate dI (H)/dH which depends on the stress of the soft magnetic material 22. Therefore, the higher harmonic wave component includes a stress information of the soft magnetic material 22.

Thereupon, the wave form of the AC electromotive force $V_2$ is frequency-analyzed using a spectrum analyzer into a basic wave component and higher harmonic wave components, and effective values Ev1 and Ev2 or distortion factor K of one or more of the higher harmonic wave components are defined as stress measurement amount of the soft magnetic materials 22.

For example, if the higher harmonic wave components are third, fifth, seventh and ninth harmonic wave components, then the effective value Ev1 is represented by the following equation (6), wherein the effective values of the third, fifth, seventh and ninth harmonic wave components are represented by $E_3$, $E_5$, $E_7$ and $E_9$, respectively.

$$E_v1 = \sqrt{E_3^2 + E_5^2 + E_7^2 + E_9^2} \tag{6}$$

When a certain harmonic wave component sufficiently and correctly includes a stress information of the soft magnetic material 22, its effective value Ev2 may singly be used as a stress measurement amount. In this case, such effective value Ev2 can be outputted by connecting a narrow-band filter corresponding to such harmonic wave component to the detecting coil 25.

The distortion factor k is represented by a following equation (7), wherein an effective value of the basic wave component is represented by $E_1$.

$$K = \frac{\sqrt{E_3^2 + E_5^2 + E_7^2 + E_9^2}}{E_1} \tag{7}$$

The distortion factor K is calculated using a calculator.

On the other hand, the magnetic characteristic of the soft magnetic material 22 is varied in response to a change in a condition in which the soft magnetic material 22 is placed. Namely, if the tension load on the soft magnetic material 22 is varied from a large value to a small value, the instantaneous magnetization rate dI (H)/dH of the soft magnetic material 22 is varied from a large value to a small value as line c→line b→line a in FIG. 5. As a result, $V_2$ (t) which is a periodic function is varied and hence, the effective value of the higher harmonic wave components is also varied.

Figure 7:
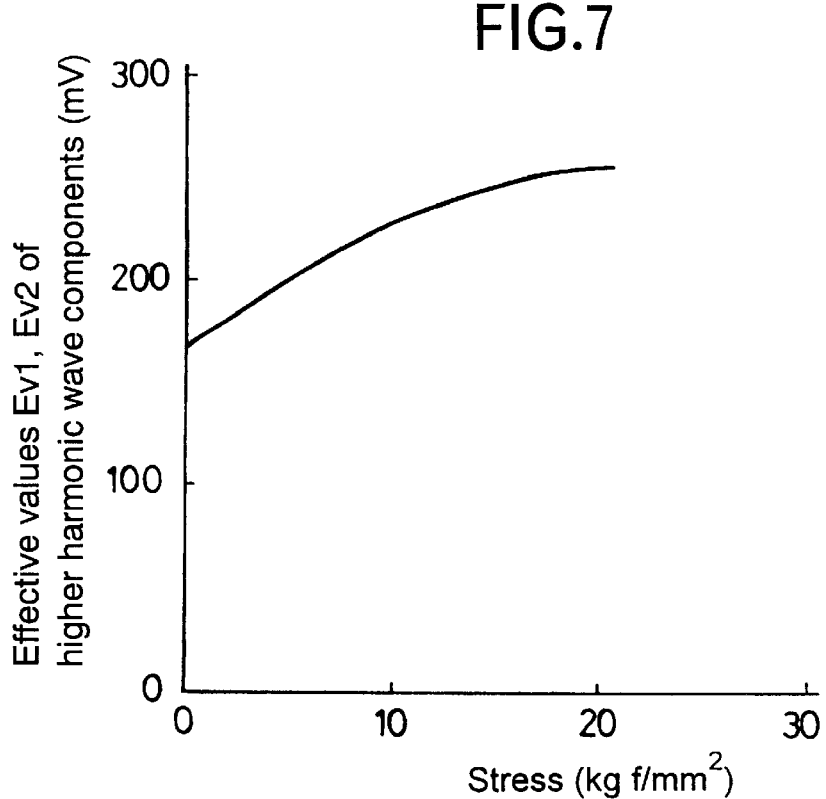
FIG. 7 is a graph illustrating the relationship between the stress and the effective values Ev1 and Ev2 of higher harmonic wave components.
Figure 8:
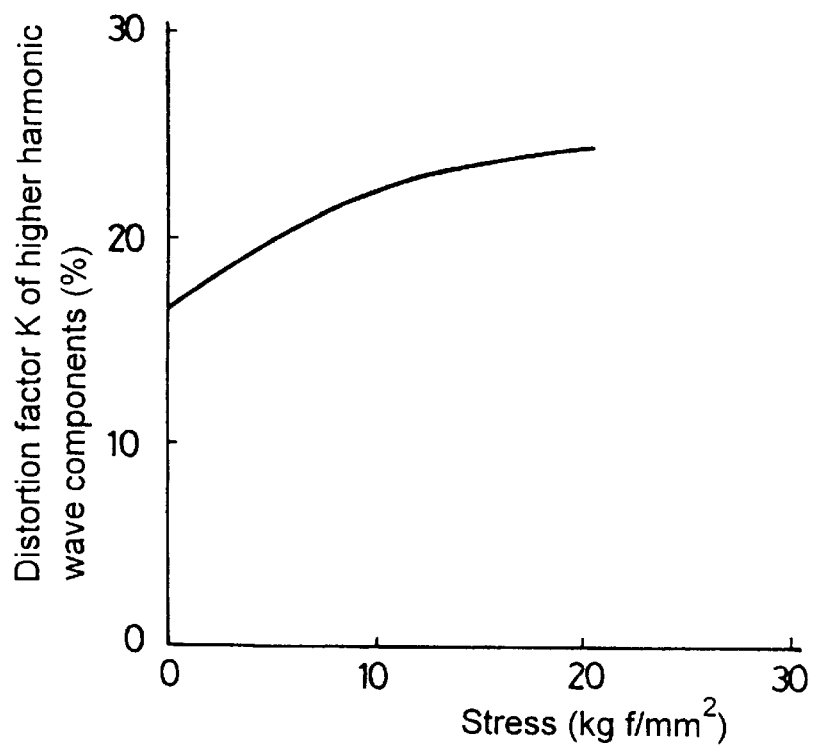
FIG. 8 is a graph illustrating the relationship between the stress and the distortion factor K of higher harmonic wave components.

Therefore, by defining the effective values Ev1 and Ev2 or the distortion factor K of the higher harmonic wave components as the measurement amounts as described above, a minute variation in stress of the soft magnetic material 22 can be correctly measured, as shown in FIGS. 7 and 8.

A particular example will be described below.

Figure 9:
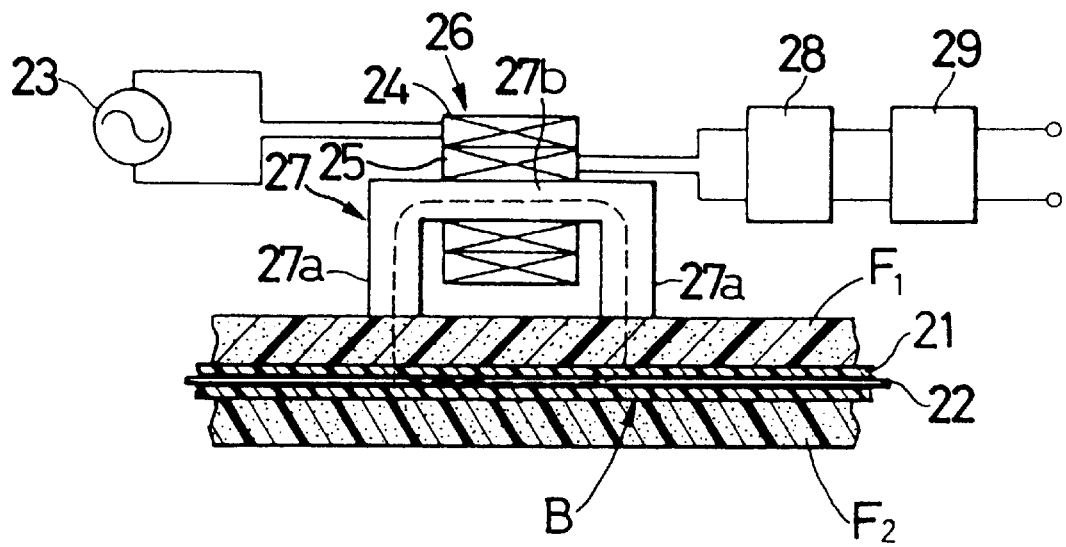
FIG. 9 is a diagrammatic illustrating a stress measuring device and a measuring process.

Two FRP members $F_1$ and $F_2$ were prepared each comprised of a reinforcing fiber which was a laminate produced by laminating eight cloths formed from carbon fibers having a diameter of 6 μm, so that the orientations of the carbon fibers in the adjacent cloths are offset by 45° from each other, wherein a matrix was formed of an epoxy resin. The size and thermal expansion coefficient of the FRP members $F_1$ and $F_2$ are identical to those described above. These FRP members $F_1$ and $F_2$ were bonded to each other in the same manner as that described above by use of the adhesive member 20 to form an adhesive layer B, as shown in FIG. 9. In this case, the soft magnetic materials 22 were likewise restrained in a tension load-applied state.

Referring to FIG. 9, a stress measuring device 26 is constructed in the following manner: A ferrite core 27 is formed into a U-shape from a pair of legs 27a, and a connecting portion 27b which connects one end of both the legs 27a to each other. The detecting coil 25 is wound 140 turns/15 mm around the connecting portion 27b, and the exciting coil 24 is wound 140 turns/15 mm around an outer periphery of the detecting coil 25. The exciting coil 24 is connected to the oscillator 23. The detecting coil 25 is connected to a spectrum analyzer 28 which is connected to a calculator 29.

First, the soft magnetic materials 22 in the adhesive layer B were subjected to a stress measurement. In measuring the stress of the soft magnetic materials 22, end faces of both the legs 27a of the core 27 were placed against one surface of the FRP member $F_1$, as shown in FIG. 9, and the oscillator 23 was operated under oscillation conditions of a frequency of a sine wave including no D.C. magnetic field component equal to 1 kHz and a voltage between peaks of 30 $V_{p-p}$, thereby applying an A.C. magnetic field H exceeding the coercive force Hc of the soft magnetic material 22 to the exciting coil 24. This caused a magnetic path to be produced between the core 27 and the soft magnetic materials 22, thereby permitting an A.C. electromotive force $V_2$ to be induced in the detecting coil 25. The A.C. electromotive force $V_2$ was inputted to the spectrum analyzer 28 and then, a distortion factor K, i.e., a value determined according to the following equation (7) mentioned above:

$$K = \frac{\sqrt{E_3^2 + E_5^2 + E_7^2 + E_9^2}}{E_1} \quad (7)$$

was outputted from the calculator 29 and defined as a stress measurement amount of the soft magnetic materials 22. When the soft magnetic material 22 is magnetized as described above, an elongation is produced in the soft magnetic material 22, namely, a magnetostriction phenomenon is generated, but the magnetostrictive oscillation phenomenon under the A.C. magnetic field is suppressed by the cured main body 21.

Then, the outer ends of both the FRP members $F_1$ and $F_2$ were clamped between chucks, and the adhesive layer B was subjected to a tension-tensile fatigue test, until the adhesive layer B was broken. During this time, the stress of the soft magnetic materials 22 was measured in every repeated stress cycle. Conditions for this fatigue test were as follows: The distance between the chucks was 150 mm; the minimum tension load was 0.14 tons; the maximum tension load was 1.4 tons; and the repetition frequency was 20 Hz.

Figure 10:
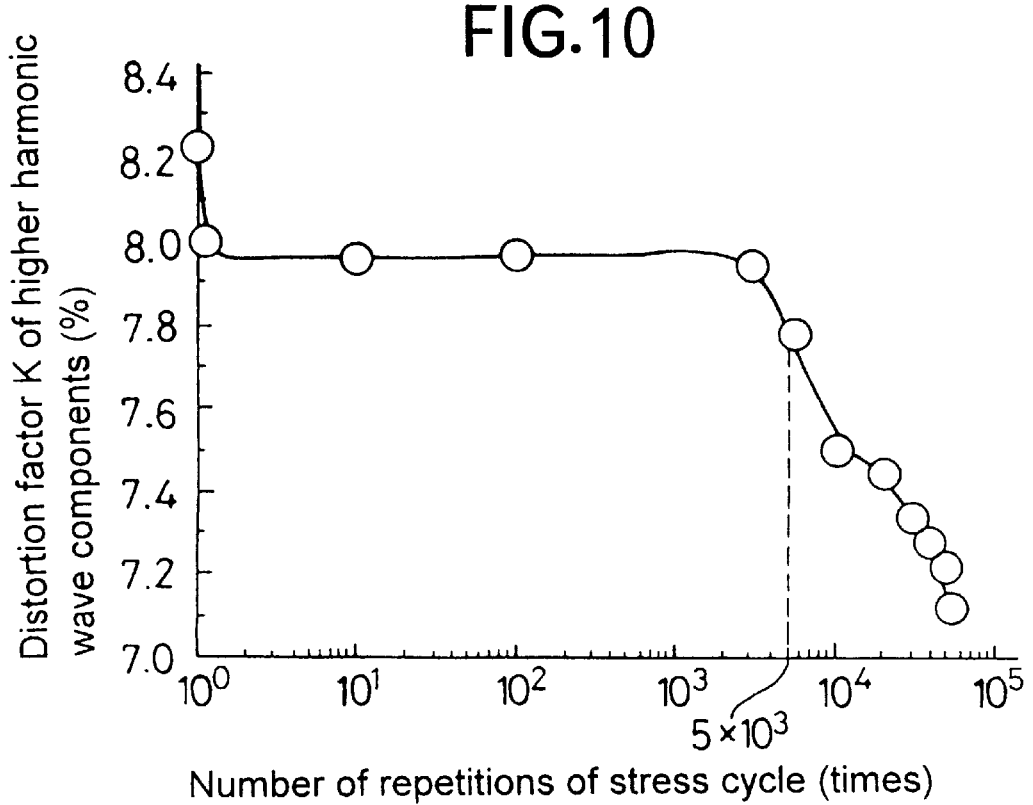
FIG. 10 is a graph illustrating one example of the relationship between the number of repetitions of stress cycle and the distortion factor K of higher harmonic wave components.

Then, the relationship between the number of repetitions of stress cycle and the distortion factor K of the high harmonic wave components was determined to provide a result shown in FIG. 10. The distortion factor K is decreased for the reason that the main body 21 is plastically deformed immediately after the start of the test, but thereafter, is constant until the number of repetitions of stress cycle reaches $2 \times 10^3$. From this, it can be seen that the adhesive layer B was not damaged. If the number of repetitions of stress cycle exceeds $2 \times 10^3$, the distortion factor K starts to decrease. This is due to the fact that the restraining force for the soft magnetic materials 22 was decreased because a damage was produced in the adhesive layer B, and due to this, the stress of the soft magnetic materials 22 was decreased, and the suppression of the magnetostrictive oscillation phenomenon was moderated under the A.C. magnetic field. The section of the adhesive layer B was observed by a microscope at the number of repetitions of stress cycle of $5 \times 10^3$ and as a result, it was confirmed that cracks were produced.

Figure 11:
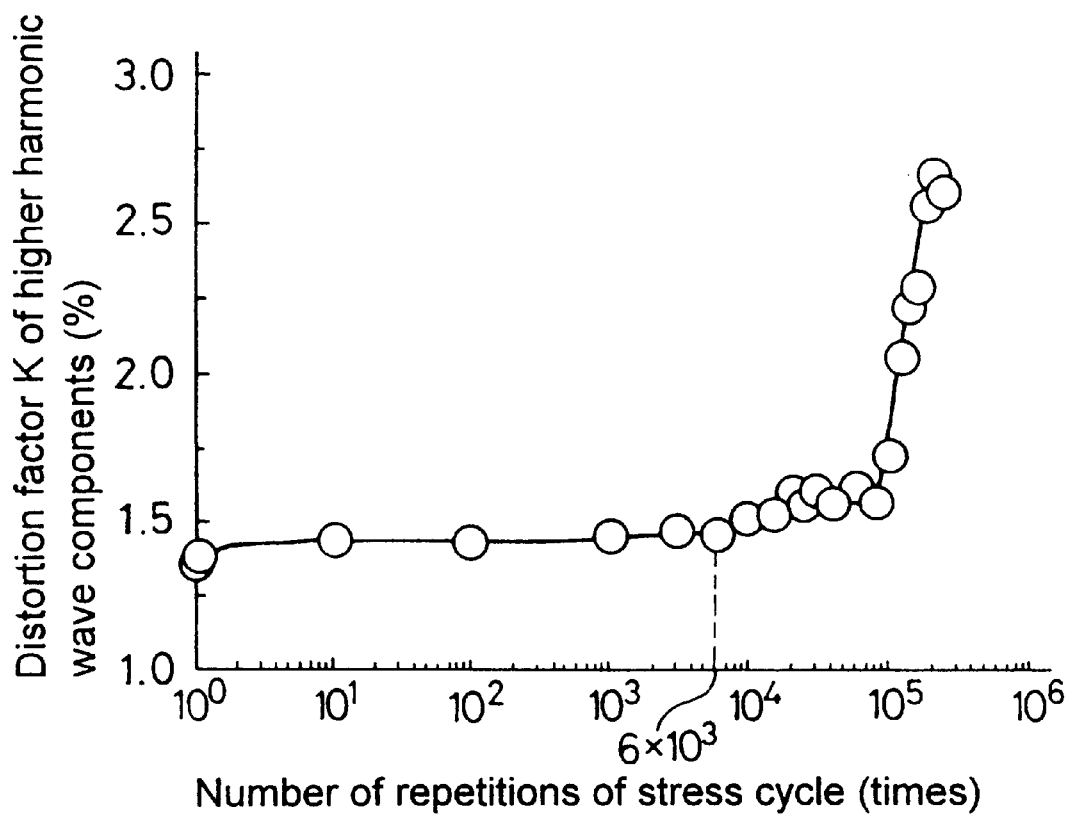
FIG. 11 is a graph illustrating another example of the relationship between the number of repetitions of stress cycle and the distortion factor K of higher harmonic wave components.

FIG. 11 shows another tension-tensile fatigue test example. In this test example, a test piece was used which was made by bonding one of the FRP members $F_1$ and a steel plate (JIS S45C having a length u of 155 mm, a width v of 25 mm, a thickness w of 4 mm and a thermal expansion coefficient of $11.2 \times 10^{-6}/°$ C.) to each other in the same manner as that described above by use of an adhesive member 20 of the above-described type. In this case, the soft magnetic materials 22 were restrained in their compression load-applied states due to the fact that the thermal expansion coefficient of the steel plate was larger than that of the FRP member $F_1$.

Conditions for this test were the same as those in the above-described test example, except that the minimum tension load was set at 0.06 tons and the maximum tension load was set at 0.55 tons. In order to enhance the sensitivity, the core 27 of the stress measuring device 26 was disposed on the side of the FRP member $F_1$.

In FIG. 11, the distortion factor K is slightly increased because the main body 21 is plastically deformed immediately after the start of the test, but thereafter, the distortion factor K is constant until the number of repetitions of stress cycle reaches $6 \times 10^3$. As a result, it can be seen that the adhesive layer B was not damaged. If the number of repetitions of stress cycle exceeds $6 \times 10^3$, the distortion factor K is started to be increased. This is due to the fact that the restraining force for the soft magnetic materials 22 was decreased because damage was produced in the adhesive layer, and due to this, the stress of the soft magnetic materials 22 was decreased and the suppression of the magnetostrictive oscillation phenomenon under the A.C. magnetic field was moderated. At the number of repetitions of stress cycle of $10^4$, the section of the adhesive layer B was observed by the microscope and as a result, it was confirmed that cracks were produced between the soft magnetic materials 22 and the cured main body 21.

A glass fiber or the like may be contained in the adhesive member 20 in order to reinforce the strength of the adhesive layer B0. Each of the members to be bonded may be formed of a metal, FRP, wood, ceramic or the like.

The stress measurement amount of the soft magnetic materials is not limited to the distortion factor K and may be a voltage between peaks, a crest value or the like in the wave form of the A.C. electromotive force.

Embodiment 2

Figure 12:
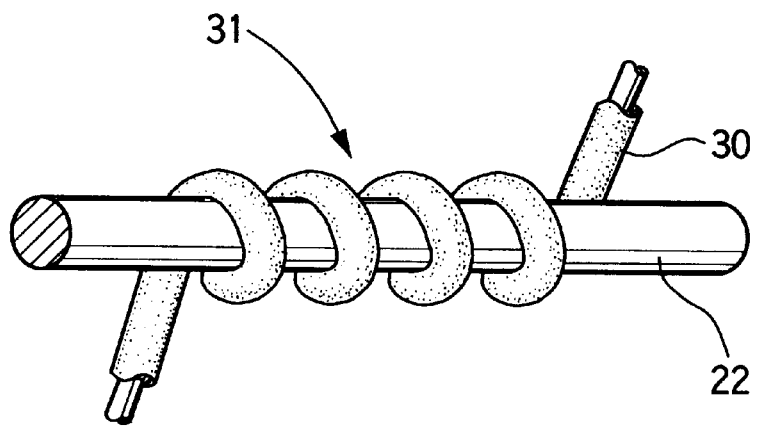
FIG. 12 is a perspective view of an essential portion of a soft magnetic material having a coated-copper wire wound therearound.

As shown in FIG. 12, a urethane-coated copper wire 30 having a diameter of 120 $\mu$m was wound at a pitch of 0.4 mm around a fibrous soft magnetic material 22 similar to those in Embodiment 1 to form a measuring coil 31.

Figure 13:
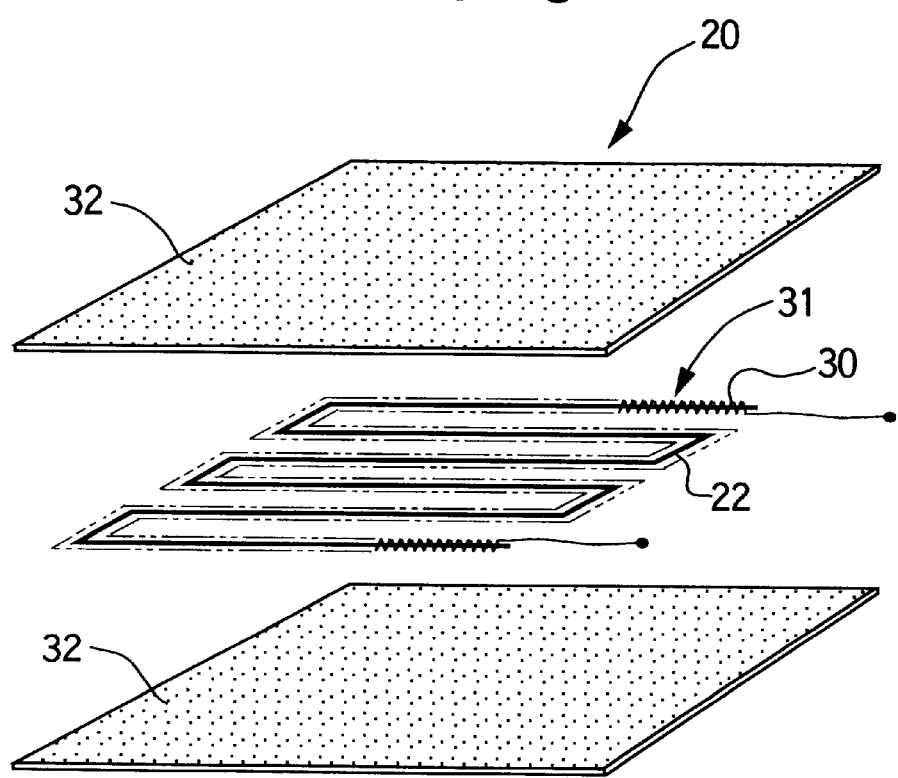
FIG. 13 is an exploded perspective view of the adhesive member.

As shown in FIG. 13, the soft magnetic material 22 having the measuring coil 31 was folded in a zigzag manner at a pitch of 1 cm, so that the folded portions form right angles. A resulting soft magnetic material was clamped between two sheets 32 having a thickness of 300 $\mu$m and formed of an uncured epoxy resin-based adhesive to produce an adhesive member 20. The adhesive member 20 had a length q of 60 mm, a width r of 25.4 mm, and a thickness n of 0.6 mm.

Figure 14:
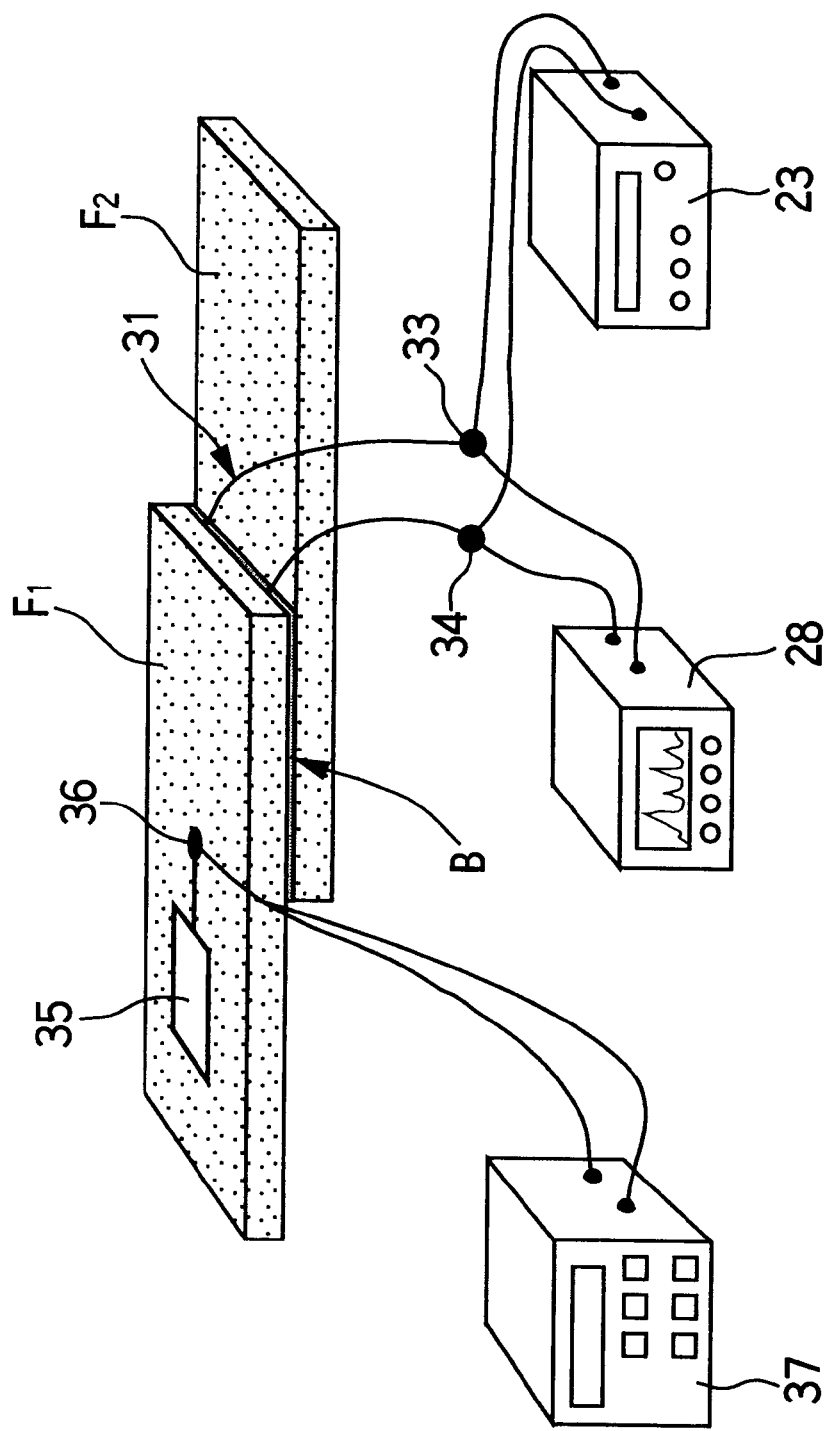
FIG. 14 is a diagrammatic illustration for explaining a stress measuring process.

As shown in FIG. 14, two plate-like FRP members $F_1$ and $F_2$ similar to those in Example 1 were prepared and bonded to each other under heating and pressurizing conditions through the adhesive member 20 to form an adhesive layer B. One terminal of each of an oscillator 23 and a spectrum analyzer 28 were connected to one terminal 33 of the measuring coil 31 extending from the adhesive layer B, and the other terminal of each of the oscillator 23 and the spectrum analyzer 28 were connected to the other terminal 34 of the measuring coil 31. A reference distortion gauge 35 was affixed to one surface of one of the FRP members $F_1$, and a data logger 37 was connected to a terminal 36 of the gauge 35.

In measuring a stress of the soft magnetic materials 22, the oscillator 23 is operated under oscillation conditions of a frequency of a sine wave including no D.C. magnetic field component equal to 5 kHz and a voltage between peaks of 10 $V_{p-p}$. Then, a voltage between both the terminals 33 and 34 was subjected to a frequency analysis by the spectrum analyzer 28 while applying a tension load to both the FRP members $F_1$ and $F_2$, thereby determining an effective value $E_3$ of a third harmonic wave component of higher harmonic components.

Figure 15:
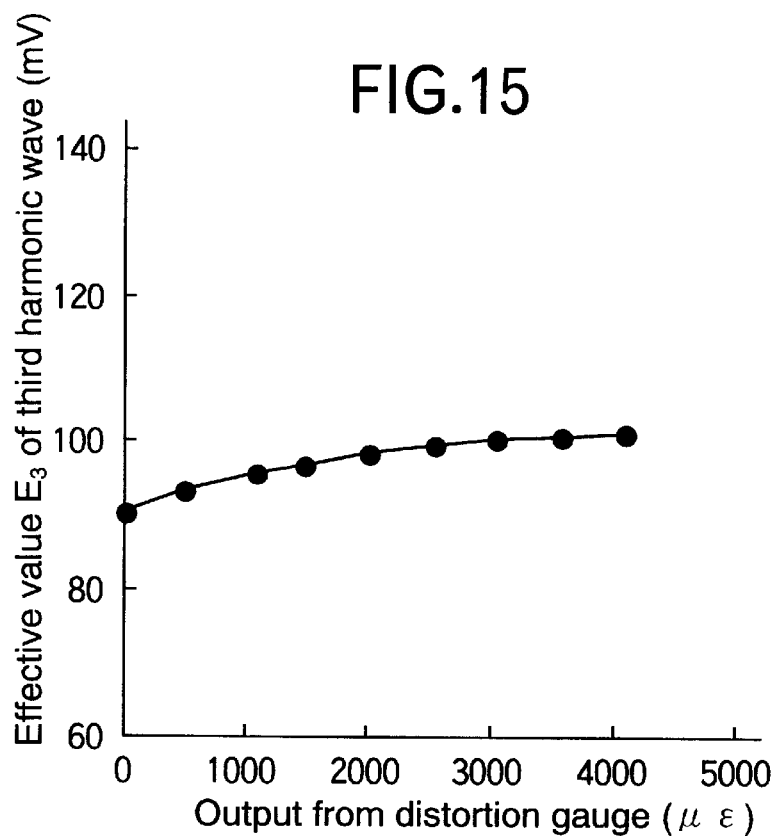
FIG. 15 is a graph illustrating the relationship between the output from a distortion gauge and the effective value $E_3$ of a third harmonic wave component.

The effective value $E_3$ of the third harmonic wave component was compared with an output from the distortion gauge to provide a result shown in FIG. 15. As is apparent from FIG. 15, the effective value $E_3$ of the third harmonic wave component was increased with an increase in output from the distortion gauge and therefore, can be used as a stress measurement amount of the stress of the soft magnetic materials 22.

Figure 16:
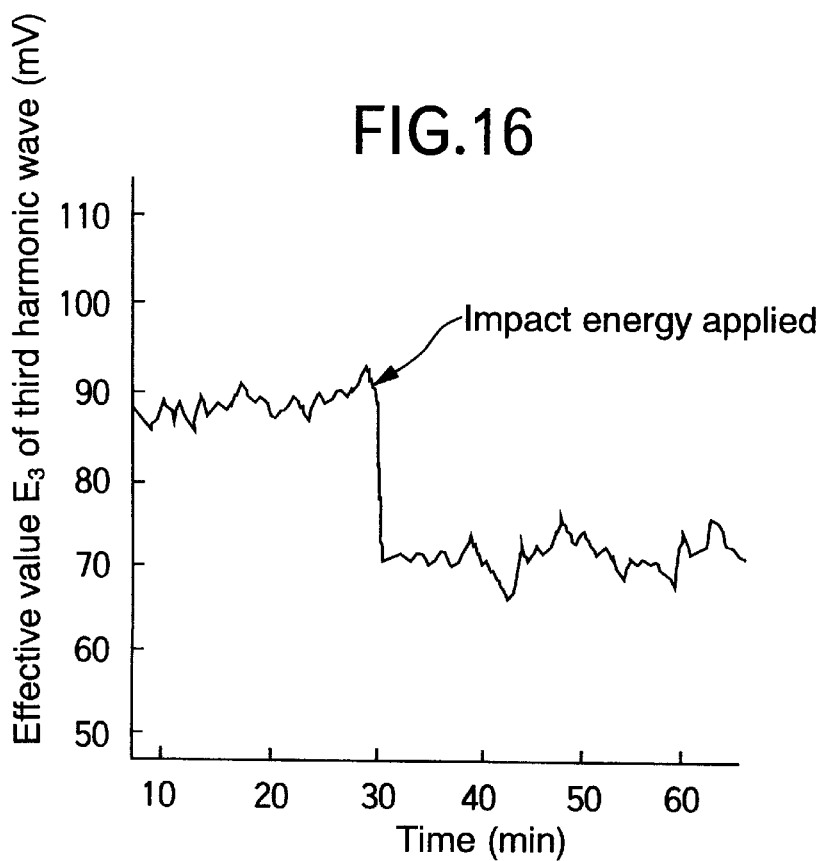
FIG. 16 is a graph illustrating the relationship between the lapsed time and the effective value $E_3$ of the third harmonic wave component.

Then, in a state in which no tension load was applied to either the FRP members $F_1$ nor $F_2$, the measurement of the stress of the soft magnetic materials 22 was continued, and after a lapse of a predetermined time, an iron sphere was dropped onto the bonded portions of the FRP members $F_1$ and $F_2$ to apply impact energy of about 30 J to the bonded portions. As a result, the effective value $E_3$ of the third harmonic wave components was decreased within a very short time, as shown in FIG. 16. From this, it can be seen that damage was produced in the adhesive layer B by the impact force.

In the adhesive member 20 shown in FIGS. 1 and 2, an urethane-coated copper wire 30 can be wound in the same manner as described above around each of the soft magnetic materials 22 to form a measuring coil 31, and an adhesive layer B similar to that described above can be formed using the adhesive member 20. In this case, the measuring coils 31 on the soft magnetic materials 22 are connected in series.

What is claimed is:

1. An adhesive member for bonding a first member to a second member by forming an adhesive layer whose internal defection can be detected by utilizing a magneto-mechanical property of soft magnetic materials, said adhesive member comprising, a main body formed of an uncured adhesive;

a plurality of soft magnetic materials embedded in said main body and restrained in an external force-applied state after curing of said main body; and a measuring coil wound around and electrically insulated from each of said soft magnetic materials and embedded in said main body.

2. An adhesive member according to claim 1, wherein said soft magnetic materials are fibrous, the fibrous soft magnetic materials being arranged parallel to each other at given distances therebetween in said main body.

3. An adhesive member according to claim 1 or 2, wherein said soft magnetic materials are formed of an amorphous metal.

4. An adhesive member for bonding one member to another member to form an adhesive layer whose internal defection can be detected by utilizing a magneto-mechanical property of a soft magnetic material, said adhesive member comprising, a main body formed of an uncured adhesive;

the soft magnetic material being of a zigzag shape embedded in said main body and restrained in an external force-applied state after curing of said main body; and a measuring coil wound around and electrically insulated from said soft magnetic material and embedded in said main body.

5. An adhesive member according to claim 4, wherein said soft magnetic material is made of an amorphous metal.

6. An adhesive member according to claim 1, wherein each of said plurality of soft magnetic materials is a separate wire, each said wire being arranged parallel to each of the other wires and spaced from each adjacent wire at the same distance in said main body.

7. An adhesive member according to claim 6, wherein each said soft magnetic material wire has a diameter p relative to the pitch m of the spacing of said wires such that $2p \leq m \leq 10p$.

8. An adhesive member according to claim 7, wherein said adhesive member has a thickness in a range of 0.03 mm to 1.0 mm, and the diameter p of said wires is in a range of 30 $\mu$m to 200 $\mu$m.

9. An adhesive member according to claim 6, wherein all of said wires lie in a single plane.

10. An adhesive member according to claim 4, wherein said zigzag shape of said soft magnetic materials are comprised of elongated segments that are substantially parallel and connected by short segments substantially perpendicular to said elongated segments at alternating ends of said elongated segments.

11. An adhesive member for bonding a first member to a second member by forming an adhesive layer whose internal defection can be detected by utilizing a magneto-mechanical property of soft magnetic materials, said adhesive member comprising, a main body formed of an uncured adhesive;

a plurality of soft magnetic materials embedded in said main body and restrained in an external force-applied state after curing of said main body, each said soft magnetic material wire has a diameter p relative to the pitch m of the spacing of said wires such that $2p \leq m \leq 10p$; and a measuring coil wound around each of said soft magnetic materials and embedded in said main body.

12. An adhesive member according to claim 11, wherein said adhesive member has a thickness in a range of 0.03 mm to 1.0 mm, and the diameter p of said wires is in a range of 30 μm to 200 μm.

13. An adhesive member according to claim 11, wherein said soft magnetic materials are fibrous, the fibrous soft magnetic materials being arranged parallel to each other at given distances therebetween in said main body.

14. An adhesive member according to claim 11, 12 or 13, wherein said soft magnetic materials are formed of an amorphous metal.

15. An adhesive member according to claim 11, wherein said plurality of soft magnetic materials are of a zigzag shape as embedded in said main body.

16. An adhesive member according to claim 11, wherein each of said plurality of soft magnetic materials is a separate wire, each said wire being arranged parallel to each of the other wires and spaced from each adjacent wire at the same distance in said main body.

17. An adhesive member according to claim 16, wherein all of said wires lie in a single plane.

18. An adhesive member according to claim 15, wherein said zigzag shape of said soft magnetic materials are comprised of elongated segments that are substantially parallel and connected by short segments substantially perpendicular to said elongated segments at alternating ends of said elongated segments.

19. An adhesive member according to claim 18, wherein said parallel elongated segments are positioned at a pitch of 1 cm.

20. An adhesive member according to claim 11 or 19, wherein said measuring coil is comprised of a coated conductive wire of substantially 120 μm diameter and is wound at a pitch of 0.4 mm.

21. An adhesive member according to claim 1, wherein said measuring coil has at opposite ends thereof terminals for connecting to detecting means.

22. An adhesive member according to claim 4, wherein said measuring coil has at opposite ends thereof terminals for connecting to detecting means.

* * * * *